US009051471B2

(12) United States Patent
Grüner et al.

(10) Patent No.: US 9,051,471 B2
(45) Date of Patent: Jun. 9, 2015

(54) WEATHER-RESISTANT PEARLESCENT PIGMENTS, PROCESS FOR THE PRODUCTION AND USE THEREOF

(75) Inventors: Michael Grüner, Auerbach (DE); Thomas Schneider, Lauf a. d. Pegnitz (DE); Günter Kaupp, Neuhaus (DE)

(73) Assignee: ECKART GMBH, Hartenstein (DE)

( * ) Notice: Subject to any disclaimer, the term of this patent is extended or adjusted under 35 U.S.C. 154(b) by 43 days.

(21) Appl. No.: 14/007,383

(22) PCT Filed: Mar. 28, 2012

(86) PCT No.: PCT/EP2012/055537
§ 371 (c)(1),
(2), (4) Date: Sep. 25, 2013

(87) PCT Pub. No.: WO2012/130897
PCT Pub. Date: Oct. 4, 2012

(65) Prior Publication Data
US 2014/0018439 A1    Jan. 16, 2014

(30) Foreign Application Priority Data

Mar. 28, 2011  (DE) .......................... 10 2011 015 338

(51) Int. Cl.
| | | |
|---|---|---|
| C09C 1/28 | (2006.01) | |
| C09C 1/00 | (2006.01) | |
| C09D 5/36 | (2006.01) | |
| C09D 11/037 | (2014.01) | |
| A61Q 1/02 | (2006.01) | |
| A61K 8/02 | (2006.01) | |
| A61K 8/19 | (2006.01) | |
| C09C 1/40 | (2006.01) | |

(52) U.S. Cl.
CPC .............. *C09C 1/28* (2013.01); *C01P 2004/60* (2013.01); *C09C 1/0021* (2013.01); *C09C 1/0024* (2013.01); *C09C 2200/1004* (2013.01); *C09C 2200/102* (2013.01); *C09C 2200/1087* (2013.01); *C09C 2200/40* (2013.01); *C09C 2200/408* (2013.01); *C09C 2220/106* (2013.01); *C09D 5/36* (2013.01); *C09D 11/037* (2013.01); *C01P 2004/61* (2013.01); *A61Q 1/02* (2013.01); *A61K 8/0258* (2013.01); *A61K 8/19* (2013.01); *A61K 2800/436* (2013.01); *C09C 1/405* (2013.01); *C01P 2004/20* (2013.01); *C01P 2006/60* (2013.01)

(58) Field of Classification Search
CPC ....................................................... C09C 1/28
See application file for complete search history.

(56) References Cited

U.S. PATENT DOCUMENTS

| | | | |
|---|---|---|---|
| 4,544,415 A | 10/1985 | Franz et al. | |
| 4,867,793 A | 9/1989 | Franz et al. | |
| 5,472,491 A | 12/1995 | Duschek et al. | |
| 5,629,400 A | 5/1997 | Standke et al. | |
| 5,679,147 A | 10/1997 | Standke et al. | |
| 5,972,098 A | 10/1999 | Andes et al. | |
| 6,176,918 B1 | 1/2001 | Glausch et al. | |
| 7,172,812 B2 | 2/2007 | Greiwe et al. | |
| 7,413,599 B2 | 8/2008 | Henglein et al. | |
| 7,611,574 B2 | 11/2009 | Kniess et al. | |
| 7,699,927 B2 | 4/2010 | Henglein et al. | |
| 8,129,021 B2 * | 3/2012 | Kaupp et al. .................. | 428/403 |
| 8,197,591 B2 | 6/2012 | Kaupp et al. | |
| 2007/0243149 A1 | 10/2007 | Hofacker et al. | |
| 2009/0056591 A1 | 3/2009 | Schmidt et al. | |
| 2009/0249979 A1 * | 10/2009 | Kaupp et al. .................. | 106/439 |
| 2010/0297045 A1 | 11/2010 | Kaupp et al. | |
| 2011/0226161 A1 | 9/2011 | Schumacher et al. | |
| 2012/0219607 A1 | 8/2012 | Schmidt et al. | |

FOREIGN PATENT DOCUMENTS

| | | |
|---|---|---|
| DE | 4321005 A1 | 1/1995 |
| DE | 19639783 A1 | 4/1998 |
| DE | 10331903 A1 | 2/2004 |
| DE | 10320455 A1 | 11/2004 |
| DE | 102004041586 A1 | 3/2006 |
| DE | 102006009129 A1 | 8/2007 |
| DE | 102006009130 A1 | 8/2007 |
| DE | 102008064202 A1 | 6/2010 |
| DE | 102009037935 A1 | 2/2011 |
| DE | 102009049413 A1 | 4/2011 |
| EP | 0141174 B1 | 8/1987 |
| EP | 0246523 A2 | 11/1987 |
| EP | 0289240 A1 | 11/1988 |

(Continued)

OTHER PUBLICATIONS

Jager et al., "Die Barriere macht den Unterschied", Farbe and Lack, Aug. 2007, p. 2-6 (corresponding English article: European Coatings Journal, May 2007, pp. 172-177 attached).

(Continued)

*Primary Examiner* — Paul Zarek
(74) *Attorney, Agent, or Firm* — The Webb Law Firm

(57) ABSTRACT

The present invention relates to a weather-resistant pearlescent pigment which consists of a platelet-shaped substrate coated with one or more highly refractive metal oxides, the platelet-shaped substrate being selected from the group consisting of synthetic mica flakes, glass flakes, $SiO_2$ flakes, $Al_2O_3$ flakes, synthetic boehmite flakes, BiOCl flakes and mixtures thereof, and a top layer, wherein the top layer consists of the following layers: a) a cerium-containing layer, selected from the group consisting of cerium oxide, cerium hydroxide, hydrated cerium oxide, and mixtures thereof, the cerium-containing layer being applied directly to the highly refractive metal oxide layer, and b) an organic-chemical compatibilizing layer, which comprises the reaction products of oligomeric silanes, wherein the oligomeric silanes have one or more amino groups, the organic-chemical compatibilizing layer being applied directly to the cerium-containing layer a).

16 Claims, No Drawings

(56) References Cited

FOREIGN PATENT DOCUMENTS

| | | | |
|---|---|---|---|
| EP | 0632109 | A1 | 1/1995 |
| EP | 0675128 | B1 | 10/1995 |
| EP | 0681009 | B1 | 11/1995 |
| EP | 0723997 | B1 | 7/1996 |
| EP | 0870730 | A1 | 10/1998 |
| EP | 0888410 | B1 | 4/2002 |
| EP | 0716127 | B1 | 7/2002 |
| EP | 1084198 | B1 | 7/2002 |
| EP | 0716128 | B1 | 12/2002 |
| EP | 0881998 | B1 | 6/2004 |
| EP | 1727864 | B1 | 7/2007 |
| EP | 1682622 | B1 | 8/2007 |
| EP | 1980594 | A1 | 6/2009 |
| EP | 2217664 | B1 | 6/2011 |
| WO | 9729059 | A1 | 8/1997 |
| WO | 9743348 | A1 | 11/1997 |
| WO | 2004056716 | A1 | 7/2004 |
| WO | 2004099319 | A2 | 11/2004 |
| WO | 2005063637 | A1 | 7/2005 |
| WO | 2007115675 | A2 | 10/2007 |

OTHER PUBLICATIONS

"Hyrdrolysis and Condensation of Organosilanes", EU 10-022/MS/fk/Sep. 1997, pp. 1-13.

Byk-Gardner, Katalog "Qualitatskontrolle fur Lacke and Kunstoffe" 2011/2012, S. 97/98.

Nancy M. Hepp et al., "Determination of total lead in lipstick: Development and validation of a microwave-assisted digestion, inductively coupled plasma-mass spectrometric method" J. Cosmet. Sci., Jul./Aug. 2009, pp. 405-414, vol. 60.

Roman Maisch, "New effect pigments from grey to black" Progress in Organic Coatings, 1993, pp. 261-272, vol. 22.

Schellenberger et al., "Schmelzvorgang unter der Lupe", Farbe & Lack, Apr. 2007, p. 130 (10 pages including partial English translation).

* cited by examiner

WEATHER-RESISTANT PEARLESCENT PIGMENTS, PROCESS FOR THE PRODUCTION AND USE THEREOF

CROSS-REFERENCE TO RELATED APPLICATIONS

The present application is the national phase of PCT/EP2012/055537 filed Mar. 28, 2012 and claims priority to German Patent Application No. 10 2011 015 338.1 filed Mar. 28, 2011, the entire disclosures of which are herein incorporated by reference.

BACKGROUND OF THE INVENTION

1. Field of the Invention

Pearlescent pigments that contain titanium dioxide in the top layer or that are made up of particulate $TiO_2$ have a degree of photocatalytic activity. If UV light acts on a pearlescent pigment in the presence of water and oxygen, the UV activity of the pearlescent pigment can trigger an accelerated decomposition of organic compounds, e.g. of a binder matrix. The proportion of UV contained in daylight can already cause this reaction, i.e. for applications such as automotive coatings which are directly exposed to the weather specially stabilized pearlescent pigments must be used. In order to counteract this adverse effect for outdoor application, pearlescent pigments can be provided with various protective coatings to reduce photoactivity. Starting from aqueous metal salt solutions, poorly soluble compounds are usually precipitated as metal oxides onto the surface of the pigments. Two different metal oxides are predominantly used here. In order to promote the compatibility of the pigments with different coatings, but in particular with the more environmentally friendly water-based systems, as a rule a further additional organic modification is made to the top layer, e.g. by means of silanes.

2. Description of Related Art

According to the teaching of EP 0 632 109 A1 a three-layered protective layer is applied to a platelet-shaped substrate coated with metal oxides. In a first step an $SiO_2$ layer is applied, in a second step a hydroxide or hydrated oxide of cerium, aluminum or zirconium is applied and in a third step at least one hydroxide or hydrated oxide of cerium, aluminum or zirconium and an organic coupling reagent are applied. This three-layered structure is disadvantageously very laborious and correspondingly cost-intensive to produce. In addition the coupling reagents have to be hydrolyzed before binding to the pigment surface, wherein however, according to the teaching of EP 0 888 410 B1, only a maximum of 60% of the added coupling reagents can be bound to the pigment surface.

EP 0 888 410 B1 discloses modified pearlescent pigments based on a platelet-shaped substrate coated with metal oxides. According to the teaching of EP 0 888 410 B1, the top layer consists of at least two oxides, a mixture of oxides, or mixed oxides of silicon dioxide, aluminum oxide, cerium oxide, titanium dioxide or zirconium dioxide and a water-based oligomeric silane. The composition of the top layer is thus also very complicated and correspondingly laborious to produce.

EP 1 682 622 B1 also discloses a top layer of two metal oxides, wherein here first a cerium oxide layer must be precipitated and subsequently an $SiO_2$ layer. Silanes are likewise predominantly used as coupling reagents.

EP 0 881 998 B1 discloses weather-resistant pearlescent pigments with a top layer either made of aluminum oxide or again of a two-layered structure of aluminum oxide and cerium oxide as well as silanes as coupling reagents.

EP 1 727 864 A1 discloses weather-resistant pearlescent pigments with a top layer made only of $SiO_2$. However, these pigments are not always completely weather-resistant in all applications, in particular in the case of optically very high-quality pigments.

0 141 174 B1 discloses weather-resistant pearlescent pigments with a top layer which contains cerium hydroxide. In this document it is proposed that this top layer be supplemented by a silicate layer and preferably by further oxide layers, such as aluminum oxide or zinc oxide, in order to guarantee a better binding of polymeric siloxanes which can function as coupling agents.

In the above-named state of the art, the UV activity of the highly refractive $TiO_2$ layer is usually suppressed by at least two different oxide layers or one mixed layer of two oxides. The use of different oxides impairs the optical properties, in particular the gloss of the pearlescent pigments. This can have a particularly detrimental effect if optically very high-quality pearlescent pigments are present, as are available nowadays as a result of the use of synthetic substrates. These relatively complex layer systems of several oxides or mixed oxides are also laborious to produce. There is an optimum pH range for the precipitation of each metal hydroxide or hydrated metal oxide. Mixed precipitations of various hydroxides or hydrated oxides therefore usually take place at pH values which represent a compromise between the optimum values for the precipitation of the pure hydroxides and that of the pure hydrated oxides. Therefore, as a rule no precipitation reactions are possible in which the conditions for the precipitation of all the inorganic components involved are optimally set in each case.

In EP 1 084 198 B1 effect pigments are described which exhibit very good adhesion to the base coat because of their surface modification with reactive orientation agents. However, EP 1 084 198 B1 discloses no weather- and UV-resistant pearlescent pigments.

The subsequent coating of pearlescent pigments with cerium hydroxide and $SiO_2$ is described in M. Jäger, U. Schmidt, "Die Barriere macht den Unterschied", Farbe and Lack August 2007, pp. 20-25. Pearlescent pigments with such a subsequent coating, unlike pearlescent pigments that have either only a cerium hydroxide or only an $SiO_2$ layer, are characterized by their good weather resistance.

SUMMARY OF THE INVENTION

In some non-limiting embodiments, the present invention provides a weather-resistant pearlescent pigment which consists of a platelet-shaped substrate coated with one or more highly refractive metal oxides, the platelet-shaped substrate being selected from the group consisting of synthetic mica flakes, glass flakes, $SiO_2$ flakes, $Al_2O_3$ flakes, synthetic boehmite flakes, BiOCl flakes and mixtures thereof, and a top layer, wherein the top layer consists of the following layers: a) a cerium-containing layer selected from the group consisting of cerium oxide, cerium hydroxide, hydrated cerium oxide and mixtures thereof, the cerium-containing layer being applied directly to the highly refractive metal oxide layer, and b) an organic-chemical compatibilizing layer, which comprises the reaction product(s) of oligomeric silanes, wherein the oligomeric silanes have one or more amino groups, the organic-chemical compatibilizing layer being applied directly to the cerium-containing layer a).

Also provided is a process for producing the above weather-resistant pearlescent pigment, comprising: a) optionally classifying the platelet-shaped substrate, obtaining substrates which have the values $D_{10}$, $D_{50}$, $D_{90}$ from the cumulative frequency distribution of the volume-averaged size distribution function with a span ΔD of from 0.7-1.4, b) suspending a platelet-shaped substrate, optionally from step a), in aqueous solution, and coating the platelet-shaped substrate with one or more highly refractive metal oxides, obtaining pearlescent pigments, c) coating the pearlescent pigments from step b) in aqueous solution with a cerium salt or a hydrolyzable cerium metalorganic compound, obtaining a layer which is selected from the group consisting of cerium hydroxide, hydrated cerium oxide and mixtures thereof, d) coating the pearlescent pigments from step c) in aqueous solution with oligomeric silanes, and e) separating the coated pearlescent pigments, optional washing with demineralized water, and drying at a temperature of from 80° to 160° C.

DETAILED DESCRIPTION

The object of the present invention is to provide a weather-resistant pearlescent pigment which does not have the above-named disadvantages of the state of the art. In particular, the weather-resistant pearlescent pigments are not to be impaired by the top layers as regards their optical properties.

The object was achieved by providing a weather-resistant pearlescent pigment which consists of a platelet-shaped substrate, coated with one or more highly refractive metal oxides, which is selected from the group consisting of synthetic mica flakes, glass flakes, $SiO_2$ flakes, $Al_2O_3$ flakes, synthetic boehmite flakes, BiOCl flakes and mixtures thereof, and a top layer, wherein the top layer consists of the following layers:
a) a cerium-containing layer, which consists of cerium oxide and/or cerium hydroxide and/or hydrated cerium oxide, and the cerium-containing layer is applied directly to the highly refractive metal oxide layer,
b) an organic-chemical compatibilizing layer, which contains or consists of the reaction products of oligomeric silanes, wherein the oligomeric silanes have one or more amino groups and the organic-chemical compatibilizing layer is applied directly to the cerium-containing layer a).

A further object was the provision of a simple and low-cost process for producing the pearlescent pigments according to the invention.

The object was achieved with a process for producing weather-resistant pearlescent pigments, which comprises the following steps:
a) optionally classifying the platelet-shaped substrate, obtaining substrates which have the values $D_{10}$, $D_{50}$, $D_{90}$ from the cumulative frequency distribution of the volume-averaged size distribution function with a span ΔD of from 0.7-1.4,
b) suspending a platelet-shaped substrate, optionally from step a), in aqueous solution and coating the platelet-shaped substrate with one or more highly refractive metal oxides, obtaining pearlescent pigments,
c) coating the pearlescent pigments from step b) in aqueous solution with a cerium salt or a hydrolyzable cerium metalorganic compound, obtaining a layer which is selected from the group consisting of cerium hydroxide, hydrated cerium oxide and mixtures thereof,
d) coating the pearlescent pigments from step c) in aqueous solution with oligomeric silanes,
e) separating the coated pearlescent pigments, optional washing with demineralized water, and drying at a temperature of from 80° to 160° C.

Substrates

The present invention is based on weather-resistant pearlescent pigments that have optically very high-quality properties. By these are meant in particular the gloss and the color purity of the pearlescent pigments in the application medium.

The pearlescent pigments according to the invention are therefore based exclusively on platelet-shaped synthetic substrates which, unlike for example natural mica flakes, have very smooth surfaces and sharp fracture edges.

The platelet-shaped substrates are therefore taken from the group consisting of synthetic mica flakes, glass flakes, $SiO_2$ flakes, $Al_2O_3$ flakes, synthetic boehmite flakes, BiOCl flakes and mixtures thereof.

The platelet-shaped synthetic substrates are preferably taken from the group consisting of synthetic mica flakes, glass flakes, $Al_2O_3$ flakes and mixtures thereof. Glass flakes and synthetic mica flakes and mixtures thereof are particularly preferred.

Such synthetic substrates are known from a series of patent applications and patents, if, for example, the platelet-shaped synthetic substrate consists of glass flakes, those produced according to the processes described in EP 0 289 240 A1, WO 2004/056716 A1 and WO 2005/063637 A1 are preferably used within the framework of this invention. The glass flakes which can be used as substrate can for example have a composition corresponding to the teaching of EP 1 980 594 B1.

Optically particularly high-quality pearlescent pigments based on synthetic substrates are known from EP 2 217 664 B1 which is hereby incorporated by reference. Here, the substrates with a narrow size distribution are disclosed, which surprisingly makes it possible to provide pearlescent pigments with particularly high color purity and high gloss.

In an embodiment the weather-resistant pearlescent pigments according to the invention have a cumulative frequency distribution of the volume-averaged size distribution function with the values $D_{10}$, $D_{50}$ and $D_{90}$, wherein this cumulative frequency distribution has a span ΔD in a range of from 0.7-1.4. The span ΔD is calculated according to Formula (I):

$$\Delta D = (D_{90} - D_{10})/D_{50} \quad (I)$$

According to the invention the span ΔD is used to characterize the particle size distribution. The smaller the span is, the narrower the particle size distribution.

In particularly preferred embodiments the weather-resistant pearlescent pigments according to the invention have a span ΔD in a range of from 0.75-1.3, further preferably in a range of from 0.8 to 1.2 and quite particularly preferably in a range of from 0.85 to 1.1.

No color-pure pearlescent pigments are obtained above a span ΔD of 1.4. Within the framework of the customary processes, pearlescent pigments below a span of the size distribution of 0.7 can only be produced very laboriously and thus no longer economically.

The weather-resistant pearlescent pigments according to the invention can have any average particle size $D_{50}$. The $D_{50}$ values of the pigments according to the invention preferably lie in a range of from 3 to 80 μm. The pigments according to the invention preferably have a $D_{50}$ value from a range of from 5 to 63 μm, particularly preferably from a range of from 7 to 56 μm and quite particularly preferably from a range of from 9 to 49 μm.

The $D_{10}$ values of the pigments according to the invention preferably lie in a range of from 1 to 25 μm. The pigments according to the invention preferably have a $D_{10}$ value from a range of from 2 to 21 μm, particularly preferably from a range of from 3 to 18 μm and quite particularly preferably from a range of from 4 to 14 μm.

The $D_{90}$ values of the pigments according to the invention preferably lie in a range of from 6 to 250 μm. The pigments according to the invention preferably have a $D_{90}$ value from a range of from 15 to 210 μm.

The $D_{10}$, $D_{50}$ or $D_{90}$ value of the cumulative frequency distribution of the volume-averaged size distribution function, as obtained by laser diffraction methods, indicates that 10%, 50% or 90% of the pigments according to the invention have a diameter which is equal to or smaller than the value indicated in each case. Here, the size distribution curve of the pigments is determined with a device from Malvern (MALVERN Mastersizer 2000) according to the manufacturer's instructions. The evaluation of the scattered light signals was carried out according to the Fraunhofer method.

The average thickness of the platelet-shaped synthetic substrates to be coated preferably lies in a range of from 50 nm to 5000 nm, preferably in a range of from 60 nm to 3000 nm and particularly preferably in a range of from 70 nm to 2000 nm.

In an embodiment the average thickness for glass flakes as substrate to be coated preferably lies in a range of from 750 nm to 1500 nm. Such glass flakes are widely available commercially. Thinner glass flakes offer further advantages. Thinner substrates lead to a smaller total layer thickness of the pigments according to the invention. Glass flakes the average thickness of which lies in a range of from 100 nm to 700 nm, further preferably in a range of from 150 nm to 600 nm, particularly preferably in a range of from 170 nm to 500 nm and quite particularly preferably in a range of from 200 nm to 400 nm, are thus also preferred.

In a further embodiment the average thickness for synthetic mica as platelet-shaped substrate to be coated preferably lies in a range of from 100 nm to 700 nm, further preferably in a range of from 120 nm to 600 nm, particularly preferably in a range of from 140 nm to 500 nm and quite particularly preferably in a range of from 150 nm to 450 nm.

If platelet-shaped synthetic substrates below an average thickness of 50 nm are coated with for example highly refractive metal oxides, extremely fragile pigments are obtained which can break apart even when incorporated into the application medium which in turn results in a significant reduction in gloss. In addition, the times for coating these thin substrates with for example highly refractive metal oxides are very long because of the large specific surface areas (surface area per weight unit of pigment) of these non-metallic platelet-shaped synthetic substrates, which gives rise to high production costs. Above an average substrate thickness of 5000 nm the pigments can be too thick overall. This can be associated with a poorer specific covering capacity, i.e. covered area per weight unit of pigment according to the invention, and a lower plane-parallel orientation in the application medium. A poorer orientation results in turn in a reduced gloss.

In a preferred embodiment the standard deviation of the thickness of the artificial substrate amounts to 15% to 100% and particularly preferably 20 to 70%. Below a standard deviation of 15% color-flop effect pigments are obtained. Above a standard deviation of 100%, much thicker pigments are contained in the entire pigment system such that poorer orientation and thus losses in gloss then result.

The average thickness is determined using a cured coating film in which the effect pigments are orientated substantially plane-parallel to the base. For this, a cross-section of the cured coating film is examined under a scanning electron microscope (SEM), wherein the thickness of at least 100 pearlescent pigments is determined and statistically averaged.

The substrates are coated with at least one highly refractive metal oxide layer in order to obtain the usual pearlescent effect based on interference. Within the framework of this invention, by a highly refractive metal oxide layer is meant a layer with a refractive index >1.8, preferably >2.0.

The at least one highly refractive layer preferably contains or consists of metal oxides, metal hydroxides and/or hydrated metal oxides from the group consisting of $TiO_2$, $Fe_2O_3$, $Fe_3O_4$, $TiFe_2O_5$, $Fe_2Ti_3O_9$, $FeTiO_3$, $ZnO$, $SnO_2$, $COO$, $Co_3O_4$, $ZrO_2$, $Cr_2O_3$ $VO_2$, $V_2O_3$, $(Sn,Sb)O_2$ and mixtures thereof. The at least one highly refractive layer particularly preferably contains or consists of metal oxides, metal hydroxides and/or hydrated metal oxides from the group consisting of $TiO_2$, $Fe_2O_3$, $Fe_3O_4$, $TiFe_2O_5$, $Fe_2Ti_3O_9$, $FeTiO_3$ and mixtures thereof.

In a further preferred embodiment the substrate is coated with only one (number: 1) highly refractive metal oxide layer from the group consisting of $TiO_2$, $Fe_2O_3$, $TiFe_2O_5$, $Fe_2Ti_3O_9$, $FeTiO_3$ and mixtures thereof.

Cerium-Containing Layer

The cerium-containing layer consists of cerium oxide and/or cerium hydroxide and/or hydrated cerium oxide. Cerium oxide forms after drying of the pigments at an increased temperature.

It has surprisingly been shown that even in very small quantities the cerium-containing layer already makes adequate UV protection possible, although in the present invention a second protective layer is dispensed with, In preferred embodiments the quantity of the cerium-containing layer lies in a range of from 0.05 to less than 0.9 wt.-%, relative to the total weight of the pearlescent pigment. The quantity of the cerium-containing layer is converted to elemental cerium, The proportion by weight should preferably be not more than 0.9 wt.-% relative to the quantity of pearlescent pigment used, as otherwise losses in the optical quality of the pigment could be too great. Moreover with quantities of more than 0.9 wt.-% a distorting yellowness becomes noticeable. In the case of the present invention the reason why this yellowness is so striking is that the pearlescent pigments according to the invention have optically very high-quality properties and even small impairments have a very distorting effect. On the other hand, below a proportion by weight of 0.05 wt.-%, as a rule the additional UV stabilization is not sufficiently pronounced. In the individual case the proportion by weight depends on the fineness and accordingly the specific surface area of the pearlescent pigment and on the layer thickness of the $TiO_2$ layer. In general, finer pigments and thicker $TiO_2$ layers also require a higher content of cerium oxide and/or cerium hydroxide and/or hydrated cerium oxide.

In particularly preferred embodiments the quantity of the cerium-containing layer lies in a range of from 0.1 to 0.7 wt.-%, further preferably in a range of from 0.2 to 0.5 wt.-%, in each case relative to the total weight of the pearlescent pigment.

The cerium oxide content of the cerium-containing layer is determined for example by means of X-ray fluorescence (XRF) analysis. For this, lithium tetraborate is added to the pigments, followed by melting in an oxidizing atmosphere and measuring as a homogeneous glass tablet. The Advantix ARL device from Thermo Scientific was used as measuring instrument. Another method for determining the cerium oxide content is XPS. In this method a depth profile of the elements of the surface coating can be obtained by sputtering. The cerium oxide content of the cerium-containing layer is preferably ascertained by means of X-ray fluorescence analysis.

In the most preferred embodiments the coating of the pearlescent pigments with the cerium-containing protective layer takes place in aqueous medium. It is assumed that in this case—in contrast to the route of deposition from organic solvents described in EP 1 682 622 B1—a better structured, more uniform protective layer is formed. It therefore also appears that only a very small amount of material is required in order to obtain a sufficient UV and weather resistance.

Water-Based, Oligomeric Silanes

Water-based, oligomeric silane is known from EP 0 675 128, EP 0 716 127 and EP 0 716 128. A use as organic compatibilizing layer for weather-resistant pearlescent pigments is known from 0 888 410 B1. These water-based, oligomeric silanes contain at least one kind of functional group. By a functional binding group is meant, within the framework of this invention, a functional group which can interact chemically with the binder. The chemical interaction can consist of a covalent bond, a hydrogen bond or an ionic interaction.

The choice of a suitable functional group depends on the chemical nature of the binder. A functional group that is chemically compatible with the functionalities of the binder is preferably chosen in order to allow good binding. This property is very important with regard to weather-resistant and UV-resistant pearlescent pigments, as a sufficiently strong adhesion between pigment and cured binder is achieved in this way. This is for example to be verified in adhesion tests such as the cross cutting test with condensation water test loads according to DIN 50 017. Passing such a test represents a necessary precondition for the use of weather-resistant pearlescent pigments in an automotive coating.

These water-based, oligomeric silanes must contain amino groups as functional groups. The amino function is a functional group which can enter into one or more chemical interactions with most groups present in binders. This can comprise a covalent bond, such as e.g. with isocyanate or carboxylate functions of the binder, or hydrogen bridge bonds such as with OH or COOR functions or also ionic interactions. An amino function is therefore very suitable for the purpose of the chemical binding of the pearlescent pigment to different types of binder.

In further preferred embodiments the water-based, oligomeric silanes have alkyl groups of from 1 to 18 C atoms. The pigment surface is partially hydrophobized by the alkyl groups, which allows a repulsion of water and a better plane-parallel orientation in the application medium. The water-based, oligomeric silanes further preferably contain alkyl groups of from 2 to 10 C atoms and particularly preferably from 3 to 6 C atoms. The alkyl groups can be linear, branched and optionally cyclic.

The water-based, oligomeric silanes are preferably produced by mixing water-soluble aminoalkylalkoxysilanes of general formula II

preferably aminopropyltriethoxysilane, aminopropylmethyldiethoxysilane, aminopropyltrimethoxysilane or aminopropylmethyldimethoxysilane, with water-insoluble alkyltrialkoxysilanes of general formula IIIa

preferably propyltrimethoxysilane, propyltriethoxysilane, methyltriethoxysilane, methyltrimethoxysilane, ethyltrimethoxysilane, ethyltriethoxysilane, isobutyltrimethoxysilane or isobutyltriethoxysilane, and/or water-insoluble dialkyldialkoxysilanes of general formula IV

preferably dimethyldimethoxysilane, dimethyldiethoxysilane, methylpropyldimethoxysilane or methylpropyldiethoxysilane, and/or mixtures of water-insoluble alkyltrialkoxysilanes and dialkyldialkoxysilanes of general formulae III and IV, wherein R is an aminofunctional organic group, $R^1$, $R^{1*}$, $R^{1}$ and $R^{1*}$ represent a methyl or ethyl radical, $R^2$ represents a linear or cyclic or branched alkyl radical with 1 to 8 C atoms, A represents an unbranched or branched alkyl radical with 1 to 3 C atoms and A' represents an unbranched or branched alkyl radical with 1 to 3 C atoms and $0<y\leq 1$, adding water to the mixture and adjusting the pH of the reaction mixture to a value between 1 and 8 and removing the alcohol already present and/or formed during the reaction.

The oligomeric silane can also be produced by mixing Q moles of water-soluble aminoalkylalkoxysilanes of general formula II R—Si($R^1$)$_y$(OR$^{1*}$)$_{3-y}$, preferably aminopropyltriethoxysilane, aminopropylmethyldiethoxysilane, aminopropyltrimethoxysilane or aminopropylmethyldimethoxysilane, with M moles of water-insoluble alkylalkoxysilanes of general formula IIIb

wherein R is an aminofunctional organic group, $R^1$, $R^{1*}$ and $R^{1**}$ represent a methyl or ethyl radical and $R^3$ represents a linear or cyclic or branched alkyl radical with 1 to 6 C atoms or a ureidoalkyl group of general formula V

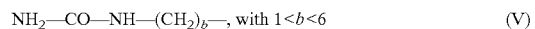

preferably b=3, and $0<y\leq 1$, in the molar ratio $0<M/Q\leq 2$, adding water to the mixture, adjusting the pH of the reaction mixture to a value between 1 and 8 and optionally removing the alcohol already present and/or formed during the reaction.

The oligomeric silane can also be obtained by mixing water-soluble organosilanes of general formula VI

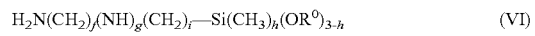

wherein $0\leq f\leq 6$, g=0 if f 0, g=1 if f>1.0$\leq i\leq 6.0\leq h\leq 1$ and $R^0$ is a methyl, ethyl, propyl or isopropyl group, preferably aminopropyltriethoxysilane, which are water-soluble but not stable in aqueous medium, with organosilanes of general formula VII

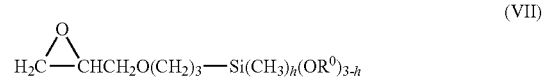

wherein $0<h\leq 1$ and $R^0$ represents a methyl, ethyl, propyl or isopropyl radical, preferably glycidyloxypropyltrimethoxysilane, and/or of general formula VIII

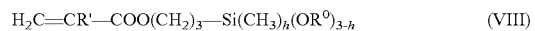

wherein $0\leq h\leq 1$, $R^0$ represents a methyl, ethyl, propyl or isopropyl radical and R' a methyl or hydrogen radical, preferably methacryloxypropyltrimethoxysilane, and a water-insoluble organosilane of general formula IX

wherein 0≤h≤1, $R^O$ represents a methyl, ethyl, propyl or isopropyl radical and R" a linear, branched or cyclic hydrocarbon radical with 1 to 8 C atoms, preferably propyltrimethoxysilane, in the molar ratio M=a/(b+c+d), wherein a is the total number of moles of organosilanes according to Formula VI, b the total number of moles of organosilanes according to Formula VII and c the total number of moles of organosilanes according to Formula VIII and d the total number of moles of organosilanes according to Formula IX, with 0≤M≤3, in particular for M equal to 0 with a equal to 0 and/or c equal to d equal to 0 and b≥1 and preferably 0.5≤M≤3, adding a water/acid mixture to the mixture,
adjusting the pH of the reaction mixture to a value between 1 and 8 and
optionally removing the alcohol already present and/or formed during the reaction.

Preferably the amount of water that is added during the distillative separation of the alcohol is equal to the amount of alcohol or alcohol/water mixture that is removed from the reaction medium. Monobasic acids are particularly suitable for adjusting the pH. Products prepared in this way also release no further alcohols through hydrolysis upon dilution with water and have a flashpoint well above 70° C.

The proportion of top layer on all of the pearlescent pigment preferably lies in a range of from 0.3 to 2.5 wt.-%, particularly preferably in a range of from 0.4 to 2.1 wt.-% and quite particularly preferably in a range of from 0.5 to 1.8 wt.-%, in each case relative to the total weight of the pearlescent pigment. This surprisingly low proportion of the entire top layer in the pearlescent pigment according to the invention can be attributed to the particularly advantageous combination of the two components.

The water-based oligomeric silanes clearly bind extremely well to the cerium-containing layer and therefore, in contrast to the state of the art, no further metal oxide layer is required in the top layer. The optical properties of the pearlescent pigment according to the invention are not impaired by the low cerium oxide content. With the help of the water-based oligomeric silane systems, groups which are insoluble or poorly soluble in water, such as for example alkyl groups of silanes, can bind without difficulty to the surface of the pearlescent pigments.

The obtained water-based oligomeric silanes (water-based organopolysiloxane-containing compositions) are substantially free of organic solvents and have a flashpoint above 70° C. As the alkoxy groups have already been substantially hydrolyzed by mixing with water, less than 5 wt.-% alcohols (methanol, ethanol) are released by hydrolysis upon dilution with water.

This results for example in compounds with the following approximate structure (Formula X)

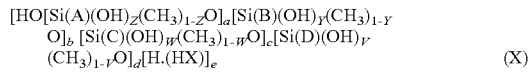

wherein
A=aminoalkyl radical derived from general formula VI,
B=glycidetheralkyl radical derived from general formula VII,
C=acryloxyalkyl or methacryloxyalkyl radical of general formula VIII,
D=alkyl radical of general formula IX,
HX=monobasic acid, wherein X=inorganic or organic acid radical, such as e.g. chloride, nitrate, formate, acetate,
v is equal to 0 or 1 and w is equal to 0 or 1 and y is equal to 0 or 1 and z is equal to 0 or 1 and a+b+c+d≥4 and a≤e≤2a, with 0≤a/(b+c+d)≤3, in particular for a/(b+c+d) is equal to 0 with a=0 and/or c is equal to d is equal to 0 and b≥1 and for 0.5≤a/(b+c+d)≤3.

The task of the silicon-functional hydroxyl groups is to form chemical bonds to the hydroxyl groups of the cerium-containing layer on the pearlescent pigment surface. A stable bond is thereby formed between silane and pigment surface.

The organofunctional groups of the oligomeric silane have the task of producing bonds to the polymer of the waterborne coating. As the oligomers can be provided with several functional groups which are different from each other, the pigment can be used in different waterborne coating systems. Being provided with methacryl and amino groups means, for example, that the pigment can be used for waterborne coating systems with polyester as polymer and for waterborne coating systems with polyurethane as polymer.

The obtained water-based oligomeric silanes (water-based organopolysiloxane-containing compositions) are advantageously substantially free of organic solvents and have a flashpoint above 70° C. As the alkoxy groups have already been substantially hydrolyzed by mixing with water, less than 5 wt-% alcohols, such as e.g. methanol or ethanol, are released through hydrolysis upon dilution with water.

Examples of water-based oligomeric silanes are aqueous, alcohol-free aminosilane hydrolyzate (Dynasylan Hydrosil 1151), aqueous, alcohol-free amino/alkylfunctional siloxane co-oligomer (Dynasylan Hydrosil 2627), aqueous, alcohol-free diamino/alkylfunctional siloxane co-oligomer (Dynasylan Hydrosil 2776), aqueous, alcohol-free amino/vinylfunctional siloxane co-oligomer (Dynasylan Hydrosil 2907), aqueous, alcohol-free amino/alkylfunctional siloxane co-oligomer (Dynasylan Hydrosil 2909), aqueous, alcohol-free amino/alkylfunctional siloxane co-oligomer (Dynasylan Hydrosil 2909, Hydrosil 2926) or aqueous, alcohol-free amino/methacrylatefunctional siloxane co-oligomer (Dynasylan Hydrosil 2929), oligomeric diaminosilane system (Dynasylan 1146).

Other silanes can also be used.

It is most preferred that the coating of the pearlescent pigments with the entire top layer takes place in aqueous medium.

Coating in aqueous medium is less expensive than in organic medium and avoids the problem of disposing of organic solvent.

Furthermore the object according to the present invention is achieved by a process for producing weather-resistant pearlescent pigments, wherein the process comprises the following steps:

a) optionally classifying the platelet-shaped substrates, obtaining substrates which have the values $D_{10}$, $D_{50}$, $D_{90}$ from the cumulative frequency distribution of the volume-averaged size distribution function with a span AD of from 0.7-1.4,
b) suspending the platelet-shaped substrates from step a) in aqueous solution,
c) coating the pearlescent pigments from step b) in aqueous solution with a cerium salt or a hydrolyzable cerium metalorganic compound obtaining a layer taken from the group consisting of cerium hydroxide, hydrated cerium oxide and mixtures thereof,
d) coating the pearlescent pigments from step c) in aqueous solution with water-based, oligomeric silanes,
e) separating the coated pearlescent pigments, optional washing with demineralized water, and drying at a temperature of from 80° to 160° C.

For precipitating the cerium-containing layer, preferred salts or hydrolyzable cerium metalorganic compounds such as cerium(III) acetate, cerium(III) acetylacetonate, cerium (III) nitrate, cerium(III) chloride, cerium(III) sulfate or cerium(IV) ammonium nitrate are used. The precipitation is carried out at a temperature of from 30° C. to 100° C., preferably 40° C. to 75° C.

The pH of this precipitation is preferably from 3 to 7 and is, if necessary, kept constant by simultaneously adding acid or lye or a suitable buffer system.

The precipitation of the water-based oligomeric silane takes place at a temperature from a range of from 75 to 80° C. and a pH from a range of from 5 to 11.

The influence of the coating on the optical properties of pearlescent pigments becomes clear in particular following condensation water loading. In a base coat/clear coat system, the condensation water test moreover makes it possible to draw conclusions about the wetting and embedding of the pearlescent pigments in the binder matrix. After loading under precisely defined conditions in the condensation water test according to DIN 50 017 (condensation water—constant climates), on the one hand the adhesion is assessed by means of the cross cutting test, as are also the optical properties, such as distinctness of image (DOI), swelling behavior or gloss, compared with an unloaded sample. Despite condensation water loading the optical properties of the pearlescent pigments according to the invention are only slightly impaired. The pearlescent pigments according to the invention also show surprisingly good results in the cross cutting test. It has been shown that the use of an oligomeric silane system on the coated pigment surface makes it much more difficult for water or moisture to penetrate the coating. It is assumed that this can be attributed to an improved combination of the degree of silane cross-linking and silane binding to the coated pigment surface. In an oligomeric silane system to be used according to the invention there is already an increased degree of silane cross-linking because of the oligomerization. A homogeneous surface modification is hereby guaranteed on the coated pigment surface. The degree of silane binding defines the binding strength between the coated pigment surface and the oligomeric silane system to be used according to the invention.

A comparison of the pearlescent pigments according to the invention with pearlescent pigments having only one cerium-containing layer clearly shows that they both exhibit a loss of their optical properties in the condensation water test and do not exhibit the desired adhesion in the cross cutting test. Surprisingly, in the condensation water test, the pearlescent pigments according to the invention display comparable or even better results than pearlescent pigments which have both a cerium-containing and an $SiO_2$ layer, which has been surface-modified with monomeric silanes, in the layer structure. The fact that the replacement of an $SiO_2$ layer surface-modified with monomeric silanes with an oligomeric silane system leads to no loss of the adhesion and optical properties under the condensation water test conditions was not foreseeable. With regard to pigments known from the state of the art, which have an $SiO_2$ layer as additional barrier layer, it was surprising that weather-resistant pigments can be obtained even without this additional barrier layer. In addition to a saving of costs in the production process, it is extremely advantageous that, by saving on one layer, pearlescent pigments can be obtained which fulfill the requirements, such as e.g. weather resistance, and the optical properties are nevertheless only marginally influenced by additional layers.

Oligomeric silane systems, compared with monomeric silanes or mixtures of monomeric silanes, have the advantage that when the oligomeric silane systems are used, a pre-crosslinked composition is applied to the coated pigment surface. When monomeric silanes are used however, because of the competitive situation between silane components and OH groups of different reactivities of the coated pigment surfaces, a coating with a variable degree of cross-linking is applied. For example it can be demonstrated that the degree of silane cross-linking of highly reactive monomeric aminosilanes such as Dynasylan AMEO can vary greatly on the coated pigment surface and therefore the surface modification can be inhomogeneous. Due to the competitive situation between the OH groups of the monomeric silanes and the reactive OH groups on the surface of the pigments to be coated, the degree of silane binding to the coated pigment surface can also vary and thus further increase the inhomogeneity of the surface modification. This inhomogeneity of the surface modification is manifest in poorer optical and adhesion properties, in particular under the condensation water test conditions.

A further, not insignificant factor, in particular for external applications and in automotive coatings, is the weathering resistance of the pigments used. In an accelerated weathering test, the pearlescent pigments according to the invention are characterized by their small deviations in color or their slight loss of gloss.

Because of the UV activity of titanium dioxide-containing pearlescent pigments, which can trigger accelerated decomposition of organic compounds, e.g. of a binder matrix, stabilized pearlescent pigments are used in external applications. In order to check the effectiveness of the stabilization, coating applications of pearlescent pigments are exposed to UV light and then measured by colorimetry in comparison with the corresponding unloaded samples. The deviation in color $\Delta E^*$ is a measure of the light fastness of the pigmented coating. The pearlescent pigments according to the invention only marginally influence the optical properties of a melamine-containing coating following UV exposure.

A subject of the invention is moreover the use of the pearlescent pigments according to the invention for the pigmentation of coatings, printing inks, plastics and cosmetics. For this, they can be used as mixtures with pigments customary in the trade, for example inorganic and organic absorption pigments, effect pigments, such as metallic effect pigments and pearlescent pigments and/or LCP pigments.

Preferred uses of the weather-resistant pearlescent pigments according to the invention are coatings, varnishes, automotive coatings, powder coatings and printing inks.

In a further embodiment the present invention comprises weather-resistant pearlescent pigments based on synthetic mica flakes which are coated with at least one highly refractive metal oxide layer and a top layer of a) a cerium-containing layer and b) an organic compatibilizing layer, and the proportion of the top layer on all of the pearlescent pigment is 0.3 to 2.5 wt.-%, relative to the total weight of the pearlescent pigment.

In a further embodiment the invention comprises weather-resistant pearlescent pigments based on glass flakes which are coated with at least one highly refractive metal oxide layer and a top layer of a) a cerium-containing layer and b) an organic compatibilizing layer, wherein the organic compatibilizing layer consists of water-based oligomeric silanes, and the silanes comprise amino groups.

EXAMPLES

The following examples are intended to explain the invention in more detail, without however limiting it. All percentages are to be understood as wt.-%.

I Production of the Pigments

Example 1

150 g of commercially available silver pearlescent pigment based on glass flakes, Luxan C001 (ECKART), was suspended in 1150 ml demineralized water and heated to 85° C. accompanied by vigorous stirring. The pH was reduced to 4.2 with dilute hydrochloric acid. A solution consisting of 1.4 g $Ce(NO_3)_3 \times 6\ H_2O$ dissolved in 40 ml demineralized water was then added. At the same time the pH was kept constant by adding a 10% NaOH solution dropwise. After all of the solution had been added, stirring continued for another hour after which the pH was adjusted to 10 with dilute caustic soda solution. 5.7 g Dynasylan 1146 diluted with 24.3 g demineralized water was then added to the suspension followed by stirring for 180 min, then the suspension was filtered off and the filter cake subsequently washed with demineralized water. The filter cake was dried under vacuum at 95° C. The pigment had a theoretical Ce content of 0.3 wt.-% relative to the total weight of the pigment. The pigment had the following particle size distribution (MALVERN Mastersizer MS 2000): $D_{10}=17.4\ \mu m$, $D_{50}=35.8\ \mu m$, $D_{90}=65.5\ \mu m$.

Example 2

100 g of commercially available silver pearlescent pigment based on synthetic mica, Symic C001 (ECKART), was suspended in 850 ml demineralized water and heated to 85° C. accompanied by vigorous stirring. The pH was lowered to 4.2 with dilute hydrochloric acid. A solution consisting of 0.93 g $Ce(NO_3)_3 \times 6\ H_2O$ dissolved in 40 ml of demineralized water was then added. At the same time the pH was kept constant by adding a 10% NaOH solution dropwise. After all of the solution had been added, stirring continued for another hour after which the pH was adjusted to 10 with dilute caustic soda solution. 5.7 g Dynasylan Hydrosil 2627 diluted with 24.3 g demineralized water was then added to the suspension followed by stirring for 180 min, then the suspension was filtered off and the filter cake subsequently washed with demineralized water. The filter cake was dried under vacuum at 95° C. The pigment had a theoretical Ce content of 0.3 wt.-%, relative to the total weight of the pigment.

The pigment had the following particle size distribution (MALVERN Mastersizer MS 2000); $D_{10}=12.0\ \mu m$, $D_{50}=23.1\ \mu m$, $D_{90}=41.6\ \mu m$.

Comparison Example 1

100 g of commercially available silver pearlescent pigment based on glass flakes, Luxan C001 (ECKART), was suspended in 500 ml isopropanol and brought to boiling point.

Accompanied by stirring, first 2.0 g $H_2O$ and then, within one hour, a solution of 0.93 g $Ce(NO_3)_3 \times 6\ H_2O$ in 8 g isopropanol were added. A solution of 0.45 g ethylenediamine in 3.0 g $H_2O$ was then added. Over a period of 2 h, 7.0 g tetraethoxysilane and 22 g isopropanol were then continuously introduced with a dosing pump (Ismatec). The suspension was then allowed to continue reacting for another 6 hours. 0.4 g Dynasylan AMEO and 1.3 g Dynasylan 9116 were then added and the mixture was allowed to cool slowly. The mixture was stirred at room temperature overnight and filtered off the next day. The pigment filter cake was then dried under vacuum at 80° C. The pigment had a theoretical Ce content of 0.3 wt.-% and an $SiO_2$ content of 1.9 wt.-%, in each case relative to the total weight of the pigment. The pigment had the following particle size distribution (MALVERN Mastersizer MS 2000): $D_{10}=17.6\ \mu m$, $D_{50}=36.0\ \mu m$, $D_{90}=66.3\ \mu m$.

Comparison Example 2

100 g of commercially available silver pearlescent pigment based on synthetic mica, Symic C001 (ECKART), was suspended in 500 isopropanol and brought to boiling point.

Accompanied by stirring, first 2.0 g $H_2O$ and then, within one hour, a solution of 0.93 g $Ce(NO_3)_3 \times 6\ H_2O$ in 8 g isopropanol were added. A solution of 0.45 g ethylenediamine in 3.0 g $H_2O$ was then added. Over a period of 2 h, 10.4 g tetraethoxysilane and 22 g isopropanol were continuously introduced with a dosing pump (Ismatec). The suspension was then allowed to continue reacting for another 6 hours. 0.4 g Dynasylan AMEO and 1.3 g Dynasylan 9116 were then added and the mixture was allowed to cool slowly. The mixture was stirred at room temperature overnight and filtered off the next day. The pigment filter cake was then dried under vacuum at 80° C. The pigment had a theoretical Ce content of 0.3 wt.-% and an $SiO_2$ content of 2.8 wt.-%, in each case relative to the total weight of the pigment. The pigment had the following particle size distribution (MALVERN Mastersizer MS 2000): $D_{10}=12.2\ \mu M$, $D_{50}=23.4\ \mu m$, $D_{90}=42.5\ \mu m$.

Comparison Example 3

Commercially available weather-resistant pearlescent pigment, Phoenix CFE 1001 (ECKART). The pigment had the following particle size distribution (MALVERN Mastersizer MS 2000): $D_{10}=9.4\ \mu m$, $D_{50}=20.8\ \mu m$, $D_{90}=39.0\ \mu m$.

Comparison Example 4

100 g of commercially available silver pearlescent pigment based on glass flakes, Luxan C001 (ECKART), was suspended in 500 ml isopropanol and brought to boiling point.

Accompanied by stirring, first 2.0 g $H_2O$ and then, within one hour, a solution of 0.93 g $Ce(NO_3)_3 \times 6\ H_2O$ in 8 g isopropanol were added. The suspension was then allowed to continue reacting for another hour. The mixture was stirred at room temperature overnight and filtered off the next day. The pigment filter cake was then dried under vacuum at 80° C. The pigment had a theoretical Ce content of 0.3 wt.-% relative to the total weight of the pigment.

The pigment had the following particle size distribution (MALVERN Mastersizer MS 2000): $D_{10}=17.5\ \mu m$, $D_{50}=35.9\ \mu m$, $D_{90}=65.7\ \mu m$.

II Characterization of the Pigments

IIa Particle Size Measurement

The size distribution curve of the platelet-shaped synthetic substrates and of the pearlescent pigments was determined with a device from Malvern (MALVERN Mastersizer 2000) according to the manufacturer's instructions. For this, approx. 0.1 g of the corresponding substrate or pigment as aqueous suspension, without addition of dispersion auxiliaries, was introduced by means of a Pasteur pipette into the sample preparation chamber of the measuring device, accompanied by constant stirring, and measured several times. The resultant average values were formed from the individual measurement results. The scattered light signals were evaluated according to the Fraunhofer method.

By the average size $D_{50}$ is meant within the framework of this invention the $D_{50}$ value of the cumulative frequency distribution of the volume-averaged size distribution function, as obtained by laser diffraction methods. The $D_{50}$ value indicates that 50% of the non-metallic platelet-shaped synthetic substrates or pigments have a diameter which is equal to or smaller than the given value, for example 20 μm. Correspondingly, the $D_{90}$ value indicates that 90% of the substrates or pigments have a diameter which is equal to or smaller than the respective value. Furthermore the $D_{10}$ value indicates that 10% of the substrates or pigments have a diameter which is equal to or smaller than the respective value.

IIb Determination of the Average Thickness of the Platelet-Shaped Synthetic Substrates In order to determine the average thickness of the non-metallic platelet-shaped synthetic substrates, the substrates or the pigments were incorporated to a level of 10 wt.-% in an Autoclear Plus HS 2K clear coat from Sikkens, using a brush and applied to a film using a spiral doctor blade (26 μm wet film thickness) and dried. After drying for 24 h, cross-sections of these doctor-blade drawdowns were prepared and measured by scanning electron microscopy. At least 100 pigment particles were measured here in order to obtain informative statistics.

IIc Determination of the Cerium Oxide Content

The cerium oxide content of the pigments was determined by means of X-ray fluorescence analysis (XFA).

For this, the pigment was incorporated into a lithium tetraborate glass tablet, fixed in solid sample measuring vessels and measured therefrom. The Advantix ARL device from Thermo Scientific was used as measuring instrument.

III Weather-Resistance of the Pigments

A Condensation Water Test

A few pigment samples were incorporated into a waterborne coating system and the test applications produced by spray painting. The base coat was overcoated with a 1K clear coat customary in the trade and then stoved. These applications were tested according to DIN 50 017 (condensation water—constant climates). The adhesion was tested by means of cross cutting according to DIN EN ISO 2409 immediately after completion of the test in comparison with the unloaded sample. Here, Gt 0 means no change and Gt 5 a very significant change.

The swelling behavior was assessed visually immediately after condensation water loading with reference to DIN 53230. Here, the value 0 means no change and the value 5 a very significant change, Finally the DOI (distinctness of image) was assessed visually. It can change as a result of the incorporation of water essentially due to the swelling processes.

TABLE 1

Condensation water results

| Sample | Gloss 20° before CW test | Gloss 20° after CW test | Loss of gloss | DOI | Immediate cross cutting | Swelling visual |
|---|---|---|---|---|---|---|
| Example 1 | 90.3 | 89.7 | <1% | 78.2 | 0 | 0 |
| Example 2 | 91.2 | 90.8 | <1% | 80.4 | 0 | 0 |
| Comparison example 1 | 94.1 | 86.6 | 8% | 70.5 | 3 | 2 |
| Comparison example 2 | 92.5 | 90.1 | 3% | 80.2 | 1 | 1 |
| Comparison example 3 | 91.3 | 88.1 | 4% | 77.6 | 1 | 2 |
| Comparison example 4 | 90.9 | 30.7 | 66% | 80.8 | 3 | 4 |

The examples according to the invention exhibited an optimum condensation water stability. All the comparison examples exhibited a significantly poorer adhesion (cross cutting) which can be explained i.e. by the use of monomeric silane systems. As the hydrolysis and condensation rates of different monomeric silanes can differ significantly (by a factor of up to 850), as described in "Hydrolysis and Condensation of organosilanes—EU 10-002/MS/fk/Sept. 97", with the use of two different silanes, as occurs in the comparison examples, it is very probable that the aminosilane hydrolyzes and/or condenses significantly earlier and can thus settle on the pigment surface first. The degree of cross-linking of the already converted aminosilane is thus also varied and the surface modification can be very inhomogeneous. Only much later does condensation occur, and thus precipitation of the alkylsilane which in this way can cover some of the introduced cross-linking groups from the aminosilane, and these are no longer available for binding to the coating system. A covering with alkylsilane, both because of the pre-coating with already converted aminosilane and because of steric hindrance due to the alkyl group, would also not be able to bind optimally to the coated pigment surface, which could explain the more pronounced swelling of the coating layer and thus less favorable intercoat adhesion.

In particular, pigment from comparison example 4 possesses no organic-chemical compatibilizing layer at all, which can explain the inadequate adhesion and also the swelling of the surrounding binder layer (gloss according to CW test).

B WOM Test

The pigment samples were incorporated into a waterborne coating system and the test applications produced by spray painting. The base coat was overcoated with a clear coat customary in the trade and then stoved. The accelerated weathering test took place according to SAE 2527 in a Q-Sun Xe 3 HS (Q-Lab) Xenon test device. The determination of the ΔE* values and grayscale classification took place in each case relative to the corresponding unloaded sample.

|  | Loss of gloss 20° after 3000 h |
|---|---|
| Example 1 | 26% |
| Comparison example 1 | 34% |

The reduction in gloss is much more pronounced in the comparison example.

C UV Resistance on Doctor-Blade Drawdowns

This test was carried out on the basis of the UV rapid test described in EP 0 870 730 in order to determine the photochemical UV activity of $TiO_2$ pigments.

For this, 1.0 g of the pearlescent pigment was dispersed in 9.0 g of a melamine-containing coating rich in double bonds. Doctor-blade drawdowns were prepared on carded paper and dried at room temperature. The doctor-blade drawdowns were divided and in each case one of the two sections was stored in the dark as an unloaded comparison sample. The samples were then irradiated with UV-containing light (UVA-340 lamp, irradiation intensity 1.0 W/m²/nm) for 150 min in a QUV device from Q-Panel. Immediately after completion of the test, color values of the loaded test pieces were ascertained relative to the respective reference sample using a CM-508i colorimeter from Minolta. The resulting ΔE* values, calculated according to the Hunter L*a*b* formula, are shown in Table 2.

In the test essentially a gray-blue discoloration of the $TiO_2$ layer of the pearlescent pigment in the doctor-blade drawdowns is observed because of Ti(III) centers formed under the influence of UV light. This is because the electron hole has physically left the $TiO_2$ and—for example due to reaction with olefinic double bonds of the binder—cannot immediately recombine with the remaining electron. As a melamine-containing coating layer significantly slows down the diffusion of water (vapor) and oxygen onto the pigment surface, there is a significant delay in reoxidation of the titanium(III) centers with the result that the graying can be measured and the ΔE value can be used as a measure for the UV resistance of the pigments. A higher ΔE* numerical value of the loaded sample relative to the unloaded reference sample thus means a lower UV resistance of the examined pigment.

TABLE 2

UV doctor-blade drawdown test results

| Sample | Precipitation medium | Layer 1 (Ce content theor.) | Layer 2 ($SiO_2$ content theor.) | ΔE* |
|---|---|---|---|---|
| Example 1 | aqueous | 0.3% Ce | — | 1.01 |
| Example 2 | aqueous | 0.3% Ce | — | 0.97 |
| Comparison example 1 | alcoholic | 0.3% Ce | 1.9% SiO2 | 2.55 |
| Comparison example 2 | alcoholic | 0.3% Ce | 2.8% SiO2 | 1.70 |
| Comparison example 3 | alcoholic | 0.4% Ce | 2.8% SiO2 | 2.01 |
| Comparison example 4 | alcoholic | 0.3% Ce | — | 2.54 |

All the comparison examples exhibited a much greater color change (ΔE*) following corresponding exposure to light. This influence can also be explained by the inadequate compatibilizing of the pigments with the corresponding coating system.
An additional $SiO_2$ layer brought no improvement in UV resistance. The use of oligomeric silane systems also proves advantageous here.

D Color Constancy and Optical Properties Compared with the Starting Material

Using doctor-blade drawdowns of the respective pigments in a conventional nitrocellulose coating (Dr. Renger Erco bronzing mixed varnish 2615e; Morton, pigmentation level of 6 wt.-%, relative to the total weight of the wet coating) on black and white opacity charts (Byko-Chart 2853, Byk Gardner) any changes in color that occurred were visually assessed. It was ascertained here that with the pearlescent pigments according to the invention no difference could be visually detected with respect to the starting material. By contrast, doctor-blade drawdowns of the pigments in the comparison examples had a grainier optical appearance compared with the starting material used in the comparison examples.

The invention claimed is:

1. A weather-resistant pearlescent pigment which consists of a platelet-shaped substrate coated with one or more metal oxides, thereby forming a metal oxide layer, wherein the metal oxide layer has a refractive index greater than 1.8, the platelet-shaped substrate being selected from the group consisting of synthetic mica flakes, glass flakes, $SiO_2$ flakes, $Al_2O_3$ flakes, synthetic boehmite flakes, BiOCl flakes and mixtures thereof, and a top layer, wherein the top layer consists of the following layers:
 a) a cerium-containing layer being applied directly to the metal oxide layer, the cerium-containing layer being selected from the group consisting of cerium oxide, cerium hydroxide, hydrated cerium oxide and mixtures thereof, and
 b) an organic-chemical compatibilizing layer being applied directly to the cerium-containing layer a), the organic-chemical compatibilizing layer comprising the reaction product(s) of one or more oligomeric silane(s), wherein the oligomeric silane(s) have one or more amino groups; and
 wherein the organic-chemical compatibilizing layer is essentially free of a separate layer of $SiO_2$.

2. The weather-resistant pearlescent pigment according to claim 1, wherein the platelet-shaped synthetic substrate is selected from the group consisting of synthetic mica flakes, glass flakes, $Al_2O_3$ flakes and mixtures thereof.

3. The weather-resistant pearlescent pigment according to claim 1, wherein the layer a) is present in quantities in a range of from 0.05 to 0.9 weight percent, relative to the total weight of the pearlescent pigment and calculated as elemental cerium.

4. The weather-resistant pearlescent pigment according to claim 1, wherein the oligomeric silane(s) have one or more alkyl groups of from 1 to 18 C atoms.

5. The weather-resistant pearlescent pigment according to claim 1, wherein the proportion of the top layer on all of the pearlescent pigment is 0.3 to 2.5 weight percent, relative to the total weight of the pearlescent pigment.

6. The weather-resistant pearlescent pigment according to claim 1, wherein the coating of the pearlescent pigment with the entire top layer has taken place in aqueous medium.

7. The weather-resistant pearlescent pigment according to claim 1, wherein the substrate is coated with one highly refractive metal oxide layer selected from the group consisting of $TiO_2$, $Fe_2O_3$, $TiFe_2O_5$, $Fe_2Ti_3O_9$, $FeTiO_3$ and mixtures thereof.

8. The weather-resistant pearlescent pigment according to claim 1, wherein the weather-resistant pearlescent pigment has the values $D_{10}$, $D_{50}$, $D_{90}$ from the cumulative frequency distribution of the volume-averaged size distribution function with a span ΔD of from 0.7-1.4, wherein the span ΔD is calculated according to Formula (I):

$$\Delta D = (D_{90} - D_{10})/D_{50} \qquad (I).$$

9. The weather-resistant pearlescent pigment according to claim 8, wherein the pearlescent pigment has a span ΔD of from 0.75-1.3.

10. A process for producing the weather-resistant pearlescent pigment according to claim 1, comprising:
 a) optionally classifying the platelet-shaped substrate, obtaining substrates which have the values $D_{10}$, $D_{50}$, $D_{90}$ from the cumulative frequency distribution of the volume-averaged size distribution function with a span ΔD of from 0.7-1.4,
 b) suspending a platelet-shaped substrate, optionally from step a), in aqueous solution, and coating the platelet-shaped substrate with one or more highly refractive metal oxides, obtaining pearlescent pigments,
 c) coating the pearlescent pigments from step b) in aqueous solution with a cerium salt or a hydrolyzable cerium metalorganic compound, obtaining a layer which is selected from the group consisting of cerium hydroxide, hydrated cerium oxide and mixtures thereof,
 d) coating the pearlescent pigments from step c) in aqueous solution with oligomeric silanes, and
 e) separating the coated pearlescent pigments, optional washing with demineralized water, and drying at a temperature of from 80° to 160° C.

11. A coating, printing ink, varnish, plastic or cosmetic comprising the weather-resistant pearlescent pigments according to claim 1.

12. The weather-resistant pearlescent pigment according to claim 1, wherein the organic-chemical compatibilizing layer consists of the reaction product(s) of one or more oligomeric silane(s), wherein the oligomeric silane(s) have one or more amino groups.

13. The weather-resistant pearlescent pigment according to claim 1, wherein the organic-chemical compatibilizing layer consists of the reaction product(s) of one or more oligomeric silane(s), wherein the oligomeric silane(s) have one or more amino groups, with one or more other silanes.

14. The weather-resistant pearlescent pigment according to claim 1, wherein the organic-chemical compatibilizing layer is free of metal oxides.

15. The weather-resistant pearlescent pigment according to claim 1, wherein the oligomeric silane is selected from the group consisting of amino/alkyl functional siloxane co-oligomer, diamino/alkyl functional siloxane co-oligomer, amino/vinyl functional siloxane co-oligomer, amino/methacrylate functional siloxane co-oligomer, oligomeric diaminosilane and mixtures thereof.

16. The weather-resistant pearlescent pigment according to claim 1, wherein the pigment is produced by a process comprising:
  a) optionally classifying the platelet-shaped substrate, obtaining substrates which have the values $D_{10}, D_{50}, D_{90}$ from the cumulative frequency distribution of the volume-averaged size distribution function with a span $\Delta D$ of from 0.7-1.4,
  b) suspending a platelet-shaped substrate, optionally from step a), in aqueous solution, and coating the platelet-shaped substrate with one or more highly refractive metal oxides, obtaining pearlescent pigments,
  c) coating the pearlescent pigments from step b) in aqueous solution with a cerium salt or a hydrolyzable cerium metalorganic compound, obtaining a layer which is selected from the group consisting of cerium hydroxide, hydrated cerium oxide and mixtures thereof,
  d) coating the pearlescent pigments from step c) in aqueous solution with one or more oligomeric silane(s), and
  e) separating the coated pearlescent pigments, optional washing with demineralized water, and drying at a temperature of from 80° to 160° C.

* * * * *